United States Patent [19]

Sanderson et al.

[11] Patent Number: 5,243,118
[45] Date of Patent: Sep. 7, 1993

[54] PROCESS FOR OLIGOMERIZING OLEFINS USING SULFATE-ACTIVATED MOLECULAR SIEVES

[75] Inventors: John R. Sanderson, Leander; John F. Knifton; Edward T. Marquis, both of Austin, all of Tex.

[73] Assignee: Texaco Chemical Company, White Plains, N.Y.

[21] Appl. No.: 803,811

[22] Filed: Dec. 9, 1991

[51] Int. Cl.$^5$ .............................................. C07C 2/12
[52] U.S. Cl. ................................... 585/515; 585/520; 585/526; 585/533
[58] Field of Search ............... 585/533, 520, 526, 515

[56] References Cited

U.S. PATENT DOCUMENTS

| | | | |
|---|---|---|---|
| 4,254,295 | 3/1981 | Tabek | 585/533 |
| 4,324,940 | 4/1982 | Dessau | 585/466 |
| 4,417,088 | 11/1983 | Miller | 585/533 |
| 4,528,414 | 7/1985 | Long et al. | 585/514 |
| 4,538,012 | 8/1985 | Miller | 585/255 |
| 4,612,406 | 9/1986 | Long et al. | 585/329 |
| 5,053,372 | 10/1991 | Brownscombe | 502/60 |

FOREIGN PATENT DOCUMENTS 261730  3/1988  European Pat. Off. .

OTHER PUBLICATIONS

D. W. Breck and R. A. Sanerson, "Molecular Sieves," Encyclopedia of Chemical Technology, Kirk-Othmer, vol. 15 (1981), pp. 638-669.

Primary Examiner—Asok Pal
Assistant Examiner—P. Achutamurthy
Attorney, Agent, or Firm—Jack H. Park; Kenneth R. Priem; Russell R. Stolle

[57] ABSTRACT

An improved process is disclosed for preparing synthetic lubricant base stocks. Synthetic lubricant base stocks are prepared in good yield by oligomerizing linear olefins using sulfate-activated molecular sieves as catalyst.

20 Claims, No Drawings

PROCESS FOR OLIGOMERIZING OLEFINS USING SULFATE-ACTIVATED MOLECULAR SIEVES

BACKGROUND OF THE INVENTION

1. Field of the Invention

The invention relates to the preparation of synthetic lubricant base stocks, and more particularly to synthetic lubricant base stocks made by oligomerizing linear olefins.

2. Description of Related Methods

Synthetic lubricants are prepared from man-made base stocks having uniform molecular structures and, therefore, well-defined properties that can be tailored to specific applications. Mineral oil base stocks, on the other hand, are prepared from crude oil and consist of complex mixtures of naturally occurring hydrocarbons. The higher degree of uniformity found in synthetic lubricants generally results in superior performance properties. For example, synthetic lubricants are characterized by excellent thermal stability. As automobile engines are reduced in size to save weight and fuel, they run at higher temperatures, therefore requiring a more thermally stable oil. Because lubricants made from synthetic base stocks have such properties as excellent oxidative/thermal stability, very low volatility, and good viscosity indices over a wide range of temperatures, they offer better lubrication, and permit longer drain intervals with less oil vaporization loss between oil changes, than mineral oil base stocks.

Synthetic base stocks may be prepared by oligomerizing internal and alpha-olefin monomers to form a mixture of dimers, trimers, tetramers, and pentamers, with minimal amounts of higher oligomers. The unsaturated oligomer products are then hydrogenated to improve their oxidative stability. The resulting synthetic base stocks have uniform isoparaffinic hydrocarbon structures similar to high quality paraffinic mineral base stocks, but have the superior properties mentioned due to their higher degree of uniformity.

Synthetic base stocks are produced in a broad range of viscosity grades. It is common practice to classify the base stocks by their viscosities, measured in centistokes (cSt) at 100° C. Those base stocks with viscosities less than or equal to about 4 cSt are commonly referred to as "low viscosity" base stocks, whereas base stocks having a viscosity in the range of around 40 to 100 cSt are commonly referred to as "high viscosity" base stocks. Base stocks having a viscosity of about 4 to about 8 cSt are referred to as "medium viscosity" base stocks. The low viscosity base stocks generally are recommended for low temperature applications. Higher temperature applications, such as motor oils, automatic transmission fluids, turbine lubricants, and other industrial lubricants, generally require higher viscosities, such as those provided by medium viscosity base stocks (i.e. 4 to 8 cSt grades). High viscosity base stocks are used in gear oils and as blending stocks.

The viscosity of a base stock is determined by the length of the oligomer molecules formed during the oligomerization reaction. The degree of oligomerization is affected by the catalyst and reaction conditions employed during the oligomerization reaction. The length of the carbon chain of the monomer starting material also has a direct influence on the properties of the oligomer products. Fluids prepared from short-chain monomers tend to have low pour points and moderately low viscosity indices, whereas fluids prepared from long-chain monomers tend to have moderately low pour points and higher viscosity indices. Oligomers prepared from long-chain monomers generally are more suitable than those prepared from shorter-chain monomers for use as medium viscosity synthetic lubricant base stocks.

One known approach to oligomerizing long-chain olefins to prepare synthetic lubricant base stocks is to contact the olefin with boron trifluoride together with a promotor at a reaction temperature sufficient to effect oligomerization of the olefin. See, for example, co-assigned U.S. Pat. Nos. 4,400,565; 4,420,646; 4,420,647; and 4,434,308. However, boron trifluoride gas ($BF_3$) is a pulmonary irritant, and breathing the gas or fumes formed by hydration of the gas with atmospheric moisture poses hazards preferably avoided. Additionally, the disposal/neutralization of $BF_3$ raises environmental concerns. Thus, a method for oligomerizing long-chain olefins using a less hazardous catalyst would be a substantial improvement in the art.

Applicants have discovered, surprisingly, that a good conversion of olefin to oligomer may be obtained by contacting olefins with sulfate-activated molecular sieves. Applicants have further discovered that an even higher conversion of olefin to oligomer may be obtained by contacting the olefin with a catalyst prepared by sulfate-activating a molecular sieve that has previously been treated to generate additional Bronsted acid sites. A higher conversion of olefin to oligomer is observed using a sulfate-activated molecular sieve than is observed using the same molecular sieve without sulfate-activation.

The process of the present invention also results in a high percentage of dimers, i.e., a high dimer to trimer ratio. A high proportion of dimers is often desirable when preparing a synthetic lubricant base stock from olefins having about 14 or more carbon atoms. In the absence of the high dimer to trimer ratio obtained using the present invention, a synthetic lubricant base stock prepared from olefins having about 14 or more carbon atoms would contain a higher percentage of high molecular weight oligomers and may have too great a viscosity for some applications. In addition to being excellent catalysts, the sulfate-activated molecular sieves used in the present invention are less hazardous and more easily handled than $BF_3$.

SUMMARY OF THE INVENTION

The invention relates to, in a process for the preparation of oligomers by contacting at elevated temperature linear olefins containing from 10 to 24 carbon atoms with a catalytically effective amount of molecular sieves, the improvement comprising sulfate-activating the molecular sieves prior to contact with the linear olefins. The invention further relates to a process for the preparation of oligomers, comprising contacting (1) linear olefins containing from 10 to 24 carbon atoms with (2) a catalytically effective amount of sulfate-activated crystalline aluminosilicate molecular sieves, at a temperature in the range of about 50° C. to about 300° C. and at a pressure of about atmospheric to about 1000 psig. The invention also relates to a process for the preparation of oligomers, comprising the steps of (a) oligomerizing linear olefins containing from 14 to 18 carbon atoms in the presence of a catalytically effective amount of crystalline aluminosilicate molecular sieves having enhanced Bronsted acidity, which crystalline aluminosilicate molecular sieves have been sulfate-activated by treatment with a sulfate-containing compound and calcined at a temperature in the range of about 500° to 800° C., wherein the olefin is oligomerized at a temperature in the range of about 120° C. to about 250° C. and at a pressure of about atmospheric to about 1000 psig, and (b) recovering oligomers of said linear olefins.

DESCRIPTION OF THE PREFERRED EMBODIMENTS

The olefin monomer feed stocks used in the present invention may be selected from compounds comprising (1) alpha-olefins having the formula R"CH=CH$_2$, where R" is an alkyl radical of 8 to 22 carbon atoms, and (2) internal olefins having the formula RCH=CHR', where R and R' are the same or different alkyl radicals of 1 to 21 carbon atoms, provided that the total number of carbon atoms in any one olefin shall be within the range of 10 to 24, inclusive. A preferred range for the total number of carbon atoms in any one olefin molecule is 12 to 18, inclusive, with an especially preferred range being 14 to 18, inclusive. Mixtures of internal and alpha-olefins may be used, as well as mixtures of olefins having different numbers of carbon atoms, provided that the total number of carbon atoms in any one olefin shall be within the range of 10 to 24, inclusive. The alpha and internal-olefins to be oligomerized in this invention may be obtained by processes wellknown to those skilled in the art and are commercially available.

The oligomerization reaction may be represented by the following general equation:

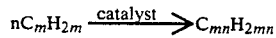

where n represents moles of monomer and m represents the number of carbon atoms in the monomer. Thus, the oligomerization of 1-tetradecene may be represented as follows:

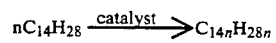

The reaction occurs sequentially. Initially, olefin monomer reacts with olefin monomer to form dimers. Some of the dimers that are formed then react with additional olefin monomers to form trimers, and so on. This results in an oligomer product distribution that varies with reaction time. As the reaction time increases, the olefin monomer conversion increases, and the selectivities for the heavier oligomers increase. Generally, each resulting oligomer contains one double bond.

The catalysts useful in the present inventive process are sulfate-activated molecular sieves. The terms "sulfate-activated" and "sulfate-activating" refer to the step of treating molecular sieves with one or more sulfate-containing compounds, as further described below. Molecular sieves suitable for sulfate-activation may be crystalline aluminosilicates, or may be essentially alumina-free silicates, such as, for example, silicalite, chromia silicates, ferrosilicates, and others.

Preferred molecular sieves are crystalline aluminosilicates having a three-dimensional interconnecting network of silica and alumina tetrahedra, belonging to a class of minerals known as zeolites. These preferred molecular sieves are complex, crystalline inorganic polymers based on an infinitely extending framework of AlO$_4$ and SiO$_4$ tetrahedra that are linked to each other by oxygen. This framework contains channels, or interconnected voids, that may be occupied by cations and by water molecules. The water molecules may be removed (reversibly), generally by the application of heat, which leaves intact a crystalline host structure permeated by micropores that may amount to 50% of the crystals by volume. Such molecular sieves may be represented by the following formula:

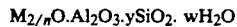

where M represents a Cation, n is the valence of the cation, y is about 2 or greater, and w represents the number of water molecules per unit cell. Further description of various aluminosilicate molecular sieves may be found in Kirk-Othmer, *Encyclopedia of Chemical Technology*, 3d. ed., vol. 15, pp. 638-669 (1981), incorporated herein by reference.

Examples of suitable commercially available molecular sieves are the Aldrich molecular sieves 3A (0.6 K$_2$O:0.40 Na$_2$O:1 Al$_2$O$_3$:2.0±0.1 SiO$_2$:x H$_2$O), having a pore diameter of about 3 Å; 4A (1 Na$_2$O:1 Al$_2$O$_3$:2.0±0.1 SiO$_2$:x H$_2$O), having a pore diameter of about 4 Å; 5A (0.80 CaO:0.20 Na$_2$O:1 Al$_2$O$_3$:2.0±0.1 SiO$_2$:x H$_2$O), having a pore diameter of about 5 Å; and 13X (1 Na$_2$O:1 Al$_2$O$_3$:2.8±0.2 SiO$_2$:x H$_2$O), having a pore diameter of about 10 Å.

Preferably, the molecular sieves to be sulfate-activated have enhanced Bronsted acidity, i.e., they have been treated to generate additional Bronsted acid sites prior to being sulfate-activated. Bronsted acidity may be introduced into the molecular sieves by decomposition of the ammonium ion-exchanged form, by hydrogen ion exchange (i.e., by washing with a mineral acid), or by hydrolysis of a zeolite containing transition metal cations.

Decomposition: Z—NH$_4$→Z—H+NH$_3$
Acid Treatment: Z—Na+H$^+$→Z—H+Na$^+$
Hydrolysis: Z—Cr$^{+++}$+H$_2$O→Z—Cr-(OH)$^{++}$+H$^+$ Suitable commercially available acid-washed molecular sieves include the Aldrich acid-washed molecular sieves AW-500, containing about 65 wt. % SiO$_2$ and about 23 wt. % Al$_2$O$_3$, or a SiO$_2$/Al$_2$O$_3$ molar ratio of about 4.8, and having a pore size of about 5 Å; and AW-300, having a pore size of about 4 Å. A commercially available activatable molecular sieve is the Linde LZ-Y52, containing about 64 wt. % SiO$_2$ and about 23 wt. % Al$_2$O$_3$, or a SiO$_2$/Al$_2$O$_3$ molar ratio of about 4.75, and having a pore size of about 8 Å. Preferably, the molecular sieves have a SiO$_2$/Al$_2$O$_3$ molar ratio greater than about 4.5.

In a preferred embodiment, the catalyst of the present inventive process is prepared by sulfate-activating molecular sieves by treatment with a sulfate-containing compound. Preferably, the sulfate-containing compound is selected from the group consisting of ammonium sulfate, ammonium hydrogen sulfate, sulfuric acid, sulfur trioxide, sulfur dioxide and hydrogen sulfide. Especially preferred sulfating agents are ammonium sulfate and sulfuric acid. Said agents may be employed neat, or as an aqueous, ketonic, alcoholic, or ether solution, but preferably as an aqueous solution. Said sulfating agents also may be employed as mixtures of the sulfating agents listed above. Excess sulfating agent may be removed by filtration.

Preferably, the sulfate-activated molecular sieves are then calcined prior to use as an oligomerization catalyst. Calcination in air or in an inert gas environment, such as nitrogen, may be conducted at a temperature of at least 100° C., but below the temperature at which thermal destruction leads to catalyst deactivation. The optimal temperature range can be determined by routine experimentation for a particular type of molecular sieve. Typically, the sulfated molecular sieves are calcined for about 1 to 24 hours at a temperature of from about 500° to 800° C. Temperatures above 900° C. should be avoided.

In a more specific embodiment, crystalline aluminosilicate molecular sieves are sulfate-activated by adding ammonium sulfate neat or, if desired, diluted with distilled water, to the molecular sieves. The slurry is then mixed for about 1 to 24 hours, filtered, washed, and calcined in a stream of air for about 1 to 24 hours. The weight percent of ammonium sulfate to crystalline aluminosilicate molecular sieve should be such that the concentration of the sulfur in the formulated catalyst (before calcination) is in the range of about 0.1 wt. % to 30 wt. %, although concentrations outside this range also may be employed.

Generally, the catalyst composition is prepared by impregnating a pre-formed pellet, extrudate or powder. A suitable procedure to be used is to immerse molecular sieve pellets in an aqueous or polar organic solvent solution of the sulfate-containing compound, preferably at ambient temperature. Higher temperatures of about 100° C. to about 150° C. may be used, if desired. This treatment should be continued, preferably with agitation, for about 0.1 to about 5 hours. The conditions should be sufficient to permit the solution to penetrate the pores of the molecular sieve. The amount of solution that is used should be adequate to permit full immersion of the molecular sieve pellets. Larger amounts of the solution can be used, if desired, but there is no particular advantage in doing so. At the end of the immersion step, the excess solution can be evaporated from the treated pellets, or the pellets can be removed from the solution and permitted to dry (e.g., in a drying oven).

The crystalline aluminosilicate molecular sieves to be sulfate-activated may be in the form of powders, pellets, spheres, shapes and extrudates. Cylindrically-shaped catalyst pellets having a diameter essentially equal to the length thereof can be employed. Diameters ranging from about 0.794 mm (1/32 inch) to about 9.525 mm (⅜ inch) possess desirable dimensions. The shape and dimensions of the pellets are not critical to the present invention; pellets of any suitable shape and dimensions may be used.

When cylindrical pellets of catalyst of the type described above are used, the liquid hourly space velocity may be varied within wide limits (e.g., 0.1 to 10) in order to obtain a desired rate of conversion. Normally, space velocities of about 0.5 to 2 LHSV will be employed.

Preferably, the pelleted catalyst compositions used in the present inventive process are employed as a fixed bed of catalyst in a continuous reaction system. In a continuous process of this nature, the time of contact of the reactants with the catalyst is one of the interrelated factors that those skilled in the art will adjust, along with temperature, pressure, bed geometry, pellet size, etc., in order to obtain a desired rate of reaction and, hence, a desired percentage of conversion of the reactants. In a continuous process, it is not necessary to drive the reaction to completion, because unreacted feedstock components may be recycled to the reactor.

The catalyst compositions of the present invention are advantageously used in a continuous process for the continuous production of oligomers from long-chain olefins. Such catalyst compositions can be used for prolonged periods without the need for regeneration. Nevertheless, with the passage of time, deactivation will tend to slowly occur. Deactivation can be measured qualitatively by the loss of olefin conversion, or as the increase of temperature required to maintain an essentially constant conversion rate for the olefin.

The oligomerization reaction may be carried out either batchwise, in a stirred slurry reactor, or continuously, in a fixed bed continuous flow reactor. The catalyst concentration should be sufficient to provide the desired catalytic effect. The temperatures at which the oligomerization may be performed are between about 50° and 300° C., with the preferred range being about 120° to 250° C., and the especially preferred range being about 160° to 180° C., for optimum conversion. At temperatures of about 200° C. or greater, the amount of unsaturation remaining in the products of the oligomerization reaction may decrease, thus reducing the degree of hydrogenation necessary to remove unsaturation from the base stocks. However, at temperatures above 200° C., the olefin conversion may decrease. The dimer to trimer ratio may increase. Applicants have found that the addition of a hydrocarbon containing a tertiary hydrogen, such as methylcyclohexane, may further reduce the amount of unsaturation present in the base stocks. One skilled in the art may choose the reaction conditions most suited to the results desired for a particular application. The reaction may be run at pressures of from 0 to 1000 psig.

Following the oligomerization reaction, the unsaturated oligomers may be hydrogenated to improve their thermal stability and to guard against oxidative degradation during their use as lubricants. The hydrogenation reaction for 1-tetradecene oligomers may be represented as follows:

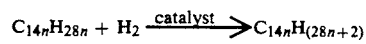

$$C_{14n}H_{28n} + H_2 \xrightarrow{\text{catalyst}} C_{14n}H_{(28n+2)}$$

where n represents moles of monomer used to form the oligomer. Hydrogenation processes known to those skilled in the art may be used to hydrogenate the oligomers. A number of metal catalysts are suitable for promoting the hydrogenation reaction, including nickel, platinum, palladium, copper, and Raney nickel. These metals may be supported on a variety of porous materials such as kieselguhr, alumina, or charcoal, or they may be formulated into a bulk metal catalyst. A particularly preferred catalyst for this hydrogenation is a nickel-copper-chromia catalyst described in U.S. Pat. No. 3,152,998, incorporated by reference herein. Other U.S. patents disclosing known hydrogenation procedures include U.S. Pat. Nos. 4,045,508; 4,013,736; 3,997,622; and 3,997,621.

Unreacted monomer may be removed either prior to or after the hydrogenation step. Optionally, unreacted monomer may be stripped from the oligomers prior to hydrogenation and recycled to the catalyst bed for oligomerization. The removal or recycle of unreacted monomer or, if after hydrogenation, the removal of non-oligomerized alkane, should be conducted under mild conditions using vacuum distillation procedures known to those skilled in the art. Distillation at temperatures exceeding 250° C. may cause the oligomers to break down in some fashion and come off as volatiles. Preferably, therefore, the reboiler or pot temperature should be kept at or under about 225° C. when stripping out the monomer. Procedures known by those skilled in the art to be alternatives to vacuum distillation also may be employed to separate unreacted components from the oligomer.

While it is known to include a distillation step after the hydrogenation procedure to obtain products of various 100° C. viscosities, it is preferred in the method of the present invention that no further distillation (beyond monomer flashing) be conducted. In other words, the monomer-stripped, hydrogenated bottoms are the desired synthetic lubricant components. Thus, the method of this invention does not require the costly, customary distillation step, yet, surprisingly, produces a synthetic lubricant component that has excellent properties and that performs in a superior fashion. However, in some contexts, one skilled in the art may find subsequent distillation useful in the practice of this invention.

The invention will be further illustrated by the following examples, which are given by way of illustration and not as limitations on the scope of this invention. The entire text of every patent, patent application or other reference mentioned above is hereby incorporated herein by reference.

EXAMPLES

In the examples detailed in the table below, the following procedures were used:

Catalysts

Catalyst 1—Aldrich molecular sieve LZ-Y52 pellets (1/16") "as is," i.e., non sulfate-activated.

Catalyst 2—Aldrich molecular sieve LZ-Y52 pellets (1/16") were placed in a crucible and covered with 10% ammonium sulfate solution. The crucible was then placed in an oven and heated to 400° C. and held at that temperature for 23 hours. A nitrogen purge was used. The sulfate-activated molecular sieves were then cooled to ambient temperature (under nitrogen), and placed in a stoppered bottle until use.

Catalyst 3—Aldrich molecular sieve AW-500 pellets (1/16") were treated according to the procedure used for Catalyst 2, above.

Catalyst 4—Aldrich molecular sieve 4A beads (1/16") were treated according to the procedure used for Catalyst 2, above.

Catalyst 5—Aldrich molecular sieve AW-300 beads (1/16") "as is," i.e., non sulfate-activated.

Catalyst 6—Aldrich molecular sieve AW-300 beads (1/16") were placed in a crucible. The crucible was then placed in an oven and heated to 500° C. and held at that temperature for 19 hours. A nitrogen purge was used. The molecular sieves were then cooled to ambient temperature (under nitrogen), and placed in a stoppered bottle until use. No ammonium sulfate was used.

Catalyst 7—Aldrich molecular sieve AW-300 beads (1/16") were placed in a crucible and covered with 10% ammonium sulfate solution. The crucible was then placed in an oven and heated to 500° C. and held at that temperature for 19 hours. A nitrogen purge was used. The sulfate-activated molecular sieves were then cooled to ambient temperature (under nitrogen), and placed in a stoppered bottle until use.

Procedure: Oligomerization of Olefins

The catalyst pellets and beads described above were ground to a fine powder. Olefin and catalyst were charged to a flask equipped with an overhead stirrer, thermometer, heating mantle, and a water-cooled condenser ($N_2$ purge). The mixture was vigorously stirred and heated to the desired temperature for the desired time. The mixture was then cooled to ambient temperature and filtered with suction. The liquid was analyzed by liquid chromatography. The results obtained are detailed in the table below.

| Ex. No. | Olefin (by carbon number) | (g) of Olefin | Catalyst | Amount of Catalyst (g) | Time/Temp. (Hr)/(°C.) | Olefin Conc. (%) | M (%) | D (%) | T+ (%) | D/T+ Ratio |
|---|---|---|---|---|---|---|---|---|---|---|
| 1 | C-14 α | 100 | Cat. 4: 4A (SA) | 10 | 5/160 | 3.0 | 97.0 | 3.0 | — | — |
| 2 | C-14 α | 100 | Cat. 3: AW-500 (SA) | 10 | 5/160 | 43.1 | 56.9 | 35.8 | 7.27 | 4.92 |
| 3 | C-14 α | 100 | Cat. 1: LZ-Y52 | 10 | 4/180 | 18.8 | 81.2 | 18.8 | — | — |
| 4 | C-14 α | 100 | Cat. 2: LZ-Y52 (SA) | 10 | 5/160 | 15.7 | 84.3 | 15.7 | — | — |
| 5 | C-14 α | 100 | Cat. 2: LZ-Y52 (SA) | 10 | 4/180 | 32.5 | 67.5 | 32.5 | — | — |
| 6 | C-14 α | 100 | Cat. 3: AW-500 (SA) | 10 | 4/180 | 48.0 | 52.0 | 41.9 | 6.10 | 6.87 |
| 7 | C-14 α | 100 | Cat. 4: 4A (SA) | 10 | 4/180 | 11.3 | 88.7 | 11.3 | — | — |
| 8 | C-14 α | 100 | Cat. 5: AW-300 | 10 | 5/160 | 19.3 | 80.7 | 16.9 | 2.41 | 7.01 |
| 9 | C-10 α | 100 | Cat. 5: AW-300 | 10 | 5/160 | 32.5 | 67.5 | 25.7 | 4.72 | 5.44 |
| 10 | C-14 α | 100 | Cat. 6: AW-300 (Calcined only) | 10 | 5/160 | 21.4 | 78.6 | 18.8 | 2.61 | 7.20 |
| 11 | C-10 α | 100 | Cat. 6: AW-300 (Calcined only) | 10 | 5/160 | 17.7 | 82.3 | 15.5 | 2.19 | 7.08 |
| 12 | C-14 α | 100 | Cat. 7: AW-300 (SA) | 10 | 5/160 | 56.2 | 43.8 | 43.5 | 12.80 | 3.40 |
| 13 | C-10 α | 100 | Cat. 7: AW-300 (SA) | 10 | 5/160 | 70.4 | 29.6 | 50.0 | 20.30 | 2.46 |

Con. = Conversion; M = Monomer; D = Dimer; and T+ = Trimer + Tetramer + Pentamer, etc.; SA = Sulfate-activated.

We claim:

1. In a process for the preparation of oligomers by contacting at elevated temperature linear olefins containing from 10 to 24 carbon atoms with a catalytically effective amount of molecular sieves, the improvement comprising sulfate-activating molecular sieves that previously have been treated to generate additional Bronsted acid sites, prior to contacting said molecular sieves with the linear olefins.

2. The process of claim 1, wherein the molecular sieves are crystalline aluminosilicate molecular sieves.

3. The process of claim 1, wherein the molecular sieves are sulfate-activated by treatment with a sulfate-containing compound, and calcined at a temperature in the range of about 500° to 800° C., prior to contact with the linear olefins.

4. The process of claim 1, wherein the molecular sieves are crystalline aluminosilicate molecular sieves, and wherein the molecular sieves are treated with a sulfate-containing compound and calcined at a temperature in the range of about 500° to 800° C. prior to contact with the linear olefins.

5. The process of claim 1, wherein the molecular sieves are sulfate-activated by treatment with a sulfate-containing compound selected from the group consisting of ammonium sulfate, ammonium hydrogen sulfate and sulfuric acid.

6. The process of claim 1, wherein the molecular sieves are sulfate-activated by treatment with a sulfate-containing compound selected from the group consisting of ammonium sulfate, ammonium hydrogen sulfate and sulfuric acid, and calcined at a temperature in the range of about 500° to 800° C., prior to contact with the linear olefins.

7. The process of claim 1, wherein said additional Bronsted acid sites of said molecular sieve were obtained by acid wash.

8. The process of claim 1, wherein said additional Bronsted acid sites of said molecular sieve were obtained by treatment with an ammonium-ion containing compound, followed by decomposition of the ammonium ion-exchanged form.

9. The process of claim 1, wherein said additional Bronsted acid sites of said molecular sieve were obtained by hydrolysis.

10. A process for the preparation of oligomers, comprising contacting (1) linear olefins containing from 10 to 24 carbon atoms with (2) a catalytically effective amount of crystalline aluminosilicate molecular sieves, which crystalline aluminosilicate molecular sieves have been acid washed to generate additional Bronsted acid sites and then sulfate-activated, wherein the olefin is oligomerized at a temperature in the range of about 50° C. to about 300° C. and at a pressure of about atmospheric to about 1000 psig.

11. The process of claim 10, wherein the temperature is in the range of about 120° C. to about 250° C.

12. The process of claim 10, wherein the crystalline aluminosilicate molecular sieves have been sulfate-activated by treatment with a sulfate-containing compound, and calcined at a temperature in the range of about 500° to 800° C., prior to contact with the linear olefins.

13. The process of claim 10, wherein the crystalline aluminosilicate molecular sieves have been sulfate-activated by treatment with a sulfate-containing compound selected from the group consisting of ammonium sulfate, ammonium hydrogen sulfate and sulfuric acid.

14. The process of claim 10, wherein the crystalline aluminosilicate molecular sieves have been sulfate-activated by treatment with a sulfate-containing compound selected from the group consisting of ammonium sulfate, ammonium hydrogen sulfate and sulfuric acid and calcined at a temperature in the range of about 500° to 800° C., prior to contact with the linear olefins.

15. The process of claim 10, wherein the olefin contains from 14 to 18 carbon atoms.

16. A process for the preparation of oligomers, comprising the steps of (a) oligomerizing linear olefins containing from 14 to 18 carbon atoms in the presence of a catalytically effective amount of crystalline aluminosilicate molecular sieves having enhanced Bronsted acidity, which crystalline aluminosilicate molecular sieves have been sulfate-activated by treatment with a sulfate-containing compound and calcined at a temperature in the range of about 500° to 800° C., wherein the olefin is oligomerized at a temperature in the range of about 120° C. to about 250° C. and at a pressure of about atmospheric to about 1000 psig, and (b) recovering oligomers of said linear olefins.

17. The process of claim 16, wherein the enhanced Bronsted acidity of the crystalline aluminosilicate molecular sieves was obtained by acid wash.

18. The process of claim 16, wherein the enhanced Bronsted acidity of the crystalline aluminosilicate molecular sieves was obtained by treatment with an ammonium-ion containing compound, followed by decomposition of the ammonium ion-exchanged form.

19. The process of claim 16, wherein the enhanced Bronsted acidity of the crystalline aluminosilicate molecular sieves was obtained by hydrolysis.

20. The process of claim 16, wherein the crystalline aluminosilicate molecular sieves have a $SiO_2/Al_2O_3$ molar ratio greater than about 4.5.

* * * * *